United States Patent [19]

Koenig

[11] Patent Number: 5,076,392
[45] Date of Patent: Dec. 31, 1991

[54] METHOD AND APPARATUS FOR FORCING A MEMBER THROUGH MATERIAL SUCH AS SOIL AND OBTAINING SAMPLES THEREFROM

[76] Inventor: Arthur S. Koenig, 3130 Mindoro, San Antonio, Tex. 78217

[21] Appl. No.: 581,181

[22] Filed: Sep. 10, 1990

Related U.S. Application Data

[63] Continuation of Ser. No. 250,321, Sep. 28, 1988, abandoned.

[51] Int. Cl.$^5$ .............................................. G01V 1/40
[52] U.S. Cl. ...................................... 181/106; 166/77; 175/171
[58] Field of Search ................. 175/20, 162, 189, 202, 175/203, 210, 1, 40, 55, 56, 171; 166/77, 249, 369, 370, 371, 104, 153; 181/102–106, 401, 0.5; 367/25, 911, 912, 191

[56] References Cited

U.S. PATENT DOCUMENTS

| | | | |
|---|---|---|---|
| 190,871 | 5/1877 | Keeley et al. | 175/162 |
| 1,318,207 | 10/1919 | Jones | 175/286 |
| 1,906,136 | 4/1933 | Dahren | 405/232 |
| 2,203,246 | 6/1940 | Zumberge et al. | 175/272 |
| 2,982,103 | 5/1961 | Revesz et al. | 405/230 |
| 3,796,055 | 3/1974 | Mahoney | 405/230 |
| 3,833,073 | 9/1974 | Carver | 175/173 |
| 3,902,326 | 9/1975 | Langenbach, Jr. | 405/230 |
| 4,070,867 | 1/1978 | Cassidy | 405/231 |
| 4,148,375 | 4/1979 | Dowler et al. | 181/117 |
| 4,207,619 | 6/1980 | Klaveness | 181/106 X |
| 4,310,066 | 1/1982 | Won | 181/121 |
| 4,387,775 | 6/1983 | Adolfsson et al. | 175/135 |
| 4,634,319 | 1/1987 | May | 405/23 |
| 4,735,280 | 4/1988 | Cole | 181/113 |

OTHER PUBLICATIONS

Atlas Piers Advertising Flyer (1986).
Magnum Pier/Slab Jack System Advertising Flyer.
Mobile Drilling Co., Inc. "Portable Minuteman" Advertising Brochure (1988).
Unknown Operator On-Site Photographs: Soil Sampler (Sep. 1988?).
Techsas Incorporated/Soiltest, Inc. Brochure Entitled "Porta-Sampler Model 417-000".

Primary Examiner—Brian S. Steinberger
Attorney, Agent, or Firm—Vaden, Eickenroht, Thompson & Boulware

[57] ABSTRACT

An apparatus for forcing a member or device, such as a sample tube or seismic or geological instrument, through a material such as soil along a selected line of action. The apparatus includes a derrick with first and second plates mounted thereto, the second plate having a locking dog extending through a hole therein for engaging a collar set in material, and the first plate being provided with a hydraulic cylinder or other device for forcing the member through the material. The first plate is also provided with an extruder head for releasably mounting the sample-containing sample tube thereto, and the hydraulic cylinder is provided with a plunger releasably mounted to the ram thereof, for extruding the sample from the sample tube.

The collar positively engages the material to provide an apparatus for transmitting the reactive forces resulting from forcing the member through the material to the material. The outer surface of the collar is shaped to approximate the shape of the hole and the collar is provided with a lip for engaging a discontinuity or groove in the wall of the hole to transmit the reactive force exerted by the force exerting apparatus to the material. The collar is also provided with a lip for engaging the locking dog. Also provided is an apparatus for removing material from the wall of the hole through the material and a method of sampling the material under a strata.

22 Claims, 6 Drawing Sheets

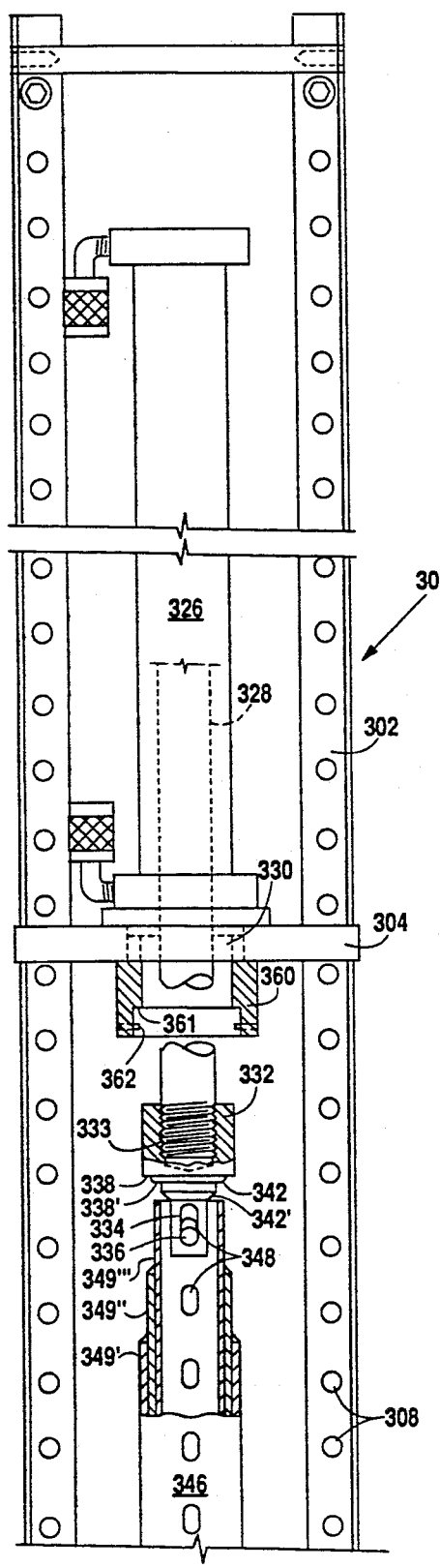
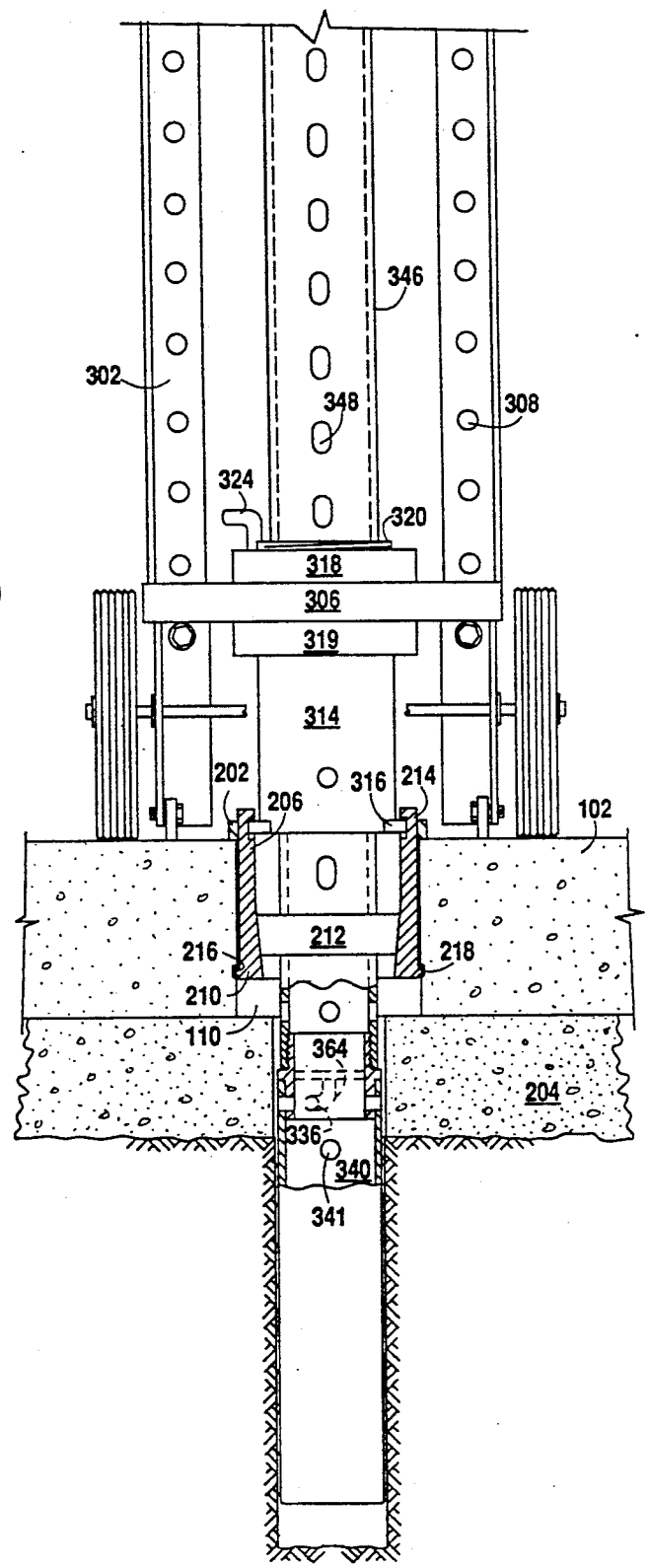
Fig. 12 A
Fig. 12 B

METHOD AND APPARATUS FOR FORCING A MEMBER THROUGH MATERIAL SUCH AS SOIL AND OBTAINING SAMPLES THEREFROM

This application is a continuation of co-pending application Ser. No. 07/250,321, filed on Sept. 28, 1988, now abandoned.

BACKGROUND OF THE INVENTION

The present invention relates to an apparatus and method for forcing a member through a material, especially where such materials exist in conjunction with a load bearing strata, either naturally occurring or man-made, and which transmits the reactive forces developed during use of the invention to the load bearing strata. More particularly, the present invention relates to a method and apparatus for obtaining material samples, such as soil samples, from under a structure or concrete slab.

A common work activity of geotechnical scientists and engineers is the analysis and evaluation of earth materials. For example, when a building structure has experienced distress to its foundation or to other elements of construction, information concerning the soils and other materials underlying the structure, as well as physical samples of those materials, is required for the analysis and evaluation of the distress.

It is well known in the geotechnical field that such samples should be "undisturbed" because sample disturbance increases the likelihood and degree of error in the assessment of in situ physical properties and characteristics of the material sampled. "Undisturbed" samples are commonly obtained by advancing a thin-walled tube, ranging in length from several inches to several feet and commonly called a "Chicago Tube" or a "Shelby Tube", into the soil or other material to be sampled. Once the tube is sufficiently advanced to contain a "plug" of the material to be sampled, it is withdrawn. That operation is repeated a sufficient number of times, using a number of such tubes, to create a continuous series of sample "plugs" which comprise the physical "undisturbed" samples of the materials through which the sample tube is forced. Upon completion of the sampling and retrieval operations, the plugs of soil are removed from the tubes and various tests performed to assess the properties of the material samples.

Although it is sometimes fairly easy to obtain such samples with truck-mounted, conventional drilling and sampling equipment, such equipment is relatively expensive to purchase and operate, and in many cases, space and other limitations, such as the need for venting the exhaust fumes of an internal combustion engine, prevent the entry of a relatively large, truck-mounted drilling rig into the location at which sampling must be conducted. Limitations of that nature are particularly acute when the sampling site happens to be within a building or other structure, for instance, when information might be required about the materials under a foundation slab after the slab has shifted or cracked. In such cases, the size of the truck-mounted drilling rig and the fumes produced by the truck's motor obviate its use and require the use of cumbersome hand-sampling methods.

Presently-utilized hand-sampling methods generally involve manually impact-driving the sample tubes into the sub-foundation materials with sledgehammers or dropweights. The sample tubes are generally attached to the end of a piece of pipe or other suitable rod for driving and, after being so driven, are extracted by manually impacting them out of the "hole" or, in some cases, using automobile jacks to jack against chains which are wrapped around the sample tube drive rod. After the samples are retrieved, they are extruded from the sample tube at a standby drill rig having extrusion capability or they are taken back to a laboratory for extrusion.

As is well known to those skilled in the art, the disadvantages of such hand-sampling techniques and equipment are many. They include, for instance, the extremely labor and equipment intensive nature of the techniques and difficulty, or even impossibility, of obtaining samples as the hardness of the sub-foundation materials increases. From an economic standpoint, only shallow samples can be obtained, and the tendency of the axis of advancement (or retraction) to wander (especially in harder materials) introduces additional variables into assessment of the samples and increases the amount of effort required. Further, even though the samples are supposed to be "undisturbed" samples, they are often severely disturbed due to the impacts required to advance and retract the sample tube. Sample quality is, therefore, unpredictable and erratic, worker fatigue is common and can be extreme, and injuries to the fingers and hands of the workers are commonplace. An additional limitation of such techniques is that they cannot be used to place various members or devices, such as penetrometers, stepped blade soil pressure transducers, piezometer tubes, and soil gas samplers for example, into the material for in situ assessment of the properties of the material because of the cumbersome nature of such techniques and the sensitivity of such members or devices to the impacts needed to advance them into the materials.

Although the above discussion refers in large part to methods for obtaining samples from beneath structures, the problems and limitations discussed are generally similar to those encountered whenever it is desired to advance or retract a device or member through a mass of material. Such operations are common in the geophysical, geological, and construction arts and include, but are not limited to, driving and the placement of members such as benchmarks, geophysical logging equipment, well points, well casings, and soil anchors for guy wires and retaining walls, as well as the penetrometers, pressure transducers, piezometer tubes, and soil gas samplers discussed above. It is, therefore, an object of the present invention to provide an apparatus which is adaptable for a number of purposes relating to advancing and retracting such a member or device(s) within a mass of material such as soil.

Further, although the above discussion refers primarily to performing an operation such as obtaining a soil sample from beneath a building foundation, it will be understood that the structure need not be a building foundation. Indeed, it is another object of the present invention to provide a small, portable device for forcing a member or device through a mass of material and which transmits the reactive forces resulting from the resistance of the material to the forcing of the member therethrough to the material or to a load bearing strata such as a concrete drain culvert, retaining wall, a naturally occurring rock foundation or other strata, or the strata found in and around the material through which the member is to be forced, as well as a floor, slab, foundation, or other elements of a building.

Further, so far as is known, no practical device or method is available for performing such operations on steeply sloped or overhead surfaces, or in enclosed or confined spaces. It is another object of the present invention to provide such an apparatus.

A further object of the present invention is to provide an apparatus which can be used to obtain tube-type soil or materials samples and to extrude those samples from the sample tube on-site, thus obviating the need for extrusion of the sample from the sample tube with a standby drill rig or at the lab, thereby enhancing the scientist's ability to direct an effective sampling program in the field.

It is another object of the present invention to provide an apparatus which can penetrate hard formations that hand-sampling methods cannot breach, can be adapted for setting benchmarks and their casings without the requirement of first drilling a pilot shaft, and can be utilized to place various devices and instruments, including, but not limited to, piezometer tubes, dutch cone penetrometers, other types of probes or bits, soil anchors, and soil pressure meters in the soil, as well as soil or other material sampling.

The advantages of such a device will be apparent to those skilled in the art from even the above-summarized brief description of the various uses and capabilities of the present invention. In short, the apparatus and method of the present invention saves time and money, eliminates manual hammer and drop weight methods, allows work in confined locations or locations that are otherwise inaccessible to conventional power equipment, and reduces the size of the crew required for performing the on-site operations necessary for the scientist or engineer to attain his or her objectives. The member can also be advanced further into the mass of materials than is currently possible with hand methods. Because the member, notably a sample tube, is smoothly forced straight into the materials worked upon, the undesirable effects of impacting, sample disturbance, and wandering of the axis of advancement are reduced. Operator fatigue is reduced and sample extrusion can be handled on-site.

SUMMARY OF THE INVENTION

To achieve the above-described objects and advantages, an apparatus is provided for forcing a member or device through a material comprising means for selecting the line of action along which a member is to be forced through a material, means mounted to the line of action selecting means for forcing the member through the material along the line of action when activated, and means for positively engaging the material through which the member is to be forced having an opening therethrough for passage of the member when the member forcing means is activated. Means is mounted to the line of action selecting means for engaging the material engaging means to transmit the reactive forces resulting from the resistance of the material to the forcing of the member therethrough upon activation of the member forcing means to the material.

The material engaging means comprises an apparatus for transmitting reactive forces to a strata or material resulting from the exertion of force along a line of action at an angle with respect to the strata or material which comprises, in a presently preferred embodiment, a collar for inserting into a hole in a strata and having an outer surface shaped to approximate the shape of the hole. The collar is provided with integral means for engaging an apparatus for exerting force along a line of action at an angle with respect to the strata in which the hole is located and means on the outside surface for engaging a groove or discontinuity in the wall of the hole to transmit the reactive force developed by the force exerting apparatus to which the collar is engaged to the material or strata in which the hole is located.

An additional aspect of the present invention is directed to an apparatus for removing material from a hole in a strata comprising a drive shaft rotatably mounted within a housing having a cutting blade mounted on one end thereof for removing material from a hole in a strata, the other end of the drive shaft being adapted for engaging power means for rotating the drive shaft. A nut is threaded onto the outside surface of the housing having means extending therefrom for supporting the housing over the hole in the strata with the cutting blade extending into the hole. The depth to which the cutting blade extends into the hole can be changed by rotation of the nut relative to the housing on the threads of the housing. Means is also provided for selectively preventing the rotation of the nut relative to the housing to maintain the cutting blade at a selected depth in the hole and to control the amount of material removed.

In another aspect of the present invention, there is provided a method of forcing a member through a material. The method includes drilling a hole in a strata, routing out a discontinuity or groove in the strata, and inserting a collar into the hole, the collar having means on the outer surface thereof for engaging the discontinuity in the wall of the hole. The member is then forced through the hole into the material, the discontinuity engaging means transmitting the reactive forces resulting from the resistance of the material to the forcing of the member therethrough to the strata.

In another aspect of the present invention, there is provided an apparatus for obtaining a soil sample. The apparatus comprises a derrick for selecting a line of action resting on a load bearing strata and having upper and lower plates mounted to the legs thereof, with a means for forcing a sample tube downwardly into the soil under the load bearing strata mounted to the upper plate. Means having an opening therethrough for passage of the sample tube when the forcing means is activated is mounted to the lower plate for positively engaging the load bearing strata to transmit reactive forces resulting from the resistance of the soil to the forcing of the sample tube therethrough upon activation of the forcing means to prevent movement of the derrick with respect to the load bearing strata.

BRIEF DESCRIPTION OF THE DRAWINGS

FIGS. 12A and 12B are partial, longitudinal sectional views of the apparatus of FIG. 6 showing the apparatus forcing a member through a material.

DETAILED DESCRIPTION OF THE INVENTION

Figure 11:
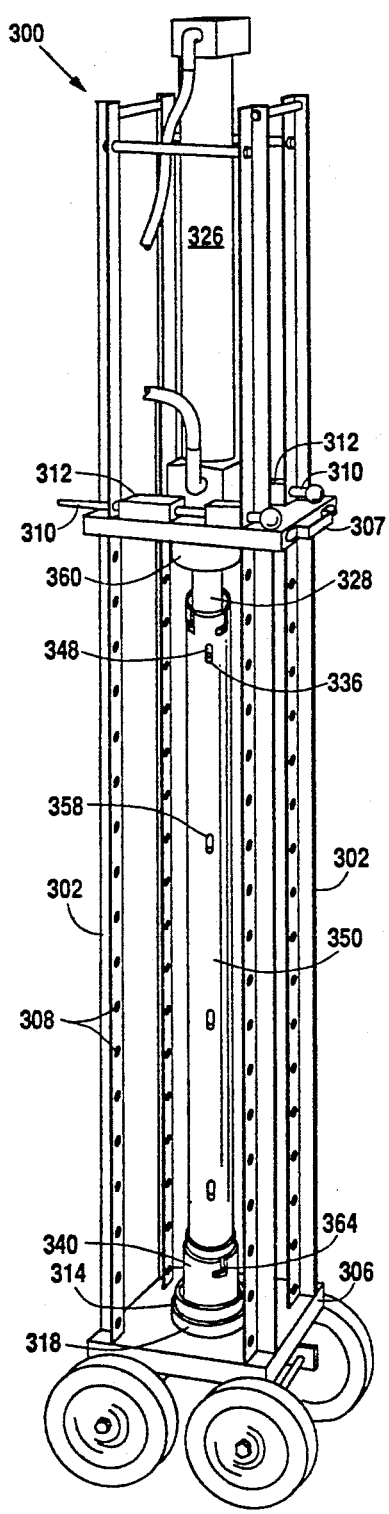
FIG. 11 is a perspective view of an apparatus constructed in accordance with the present invention for forcing a member through a material.
Figure 1:
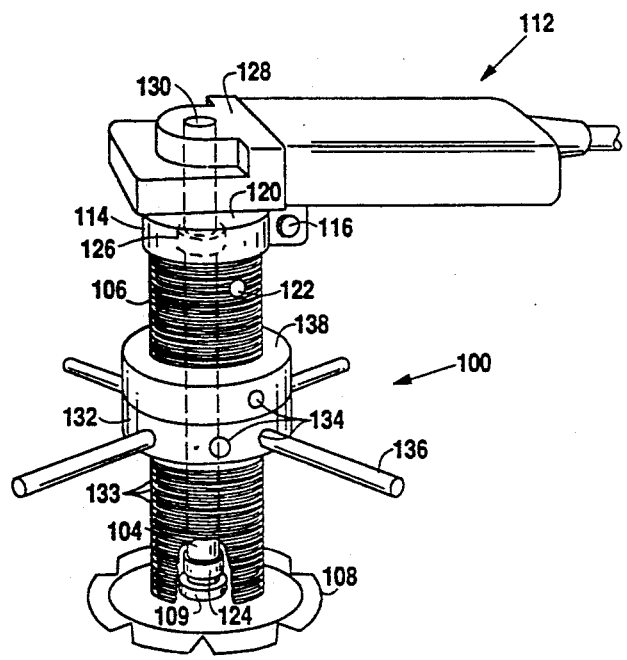
FIG. 1 is a perspective view of an apparatus constructed in accordance with the present invention for removing material from a hole in a strata.
Figure 6:
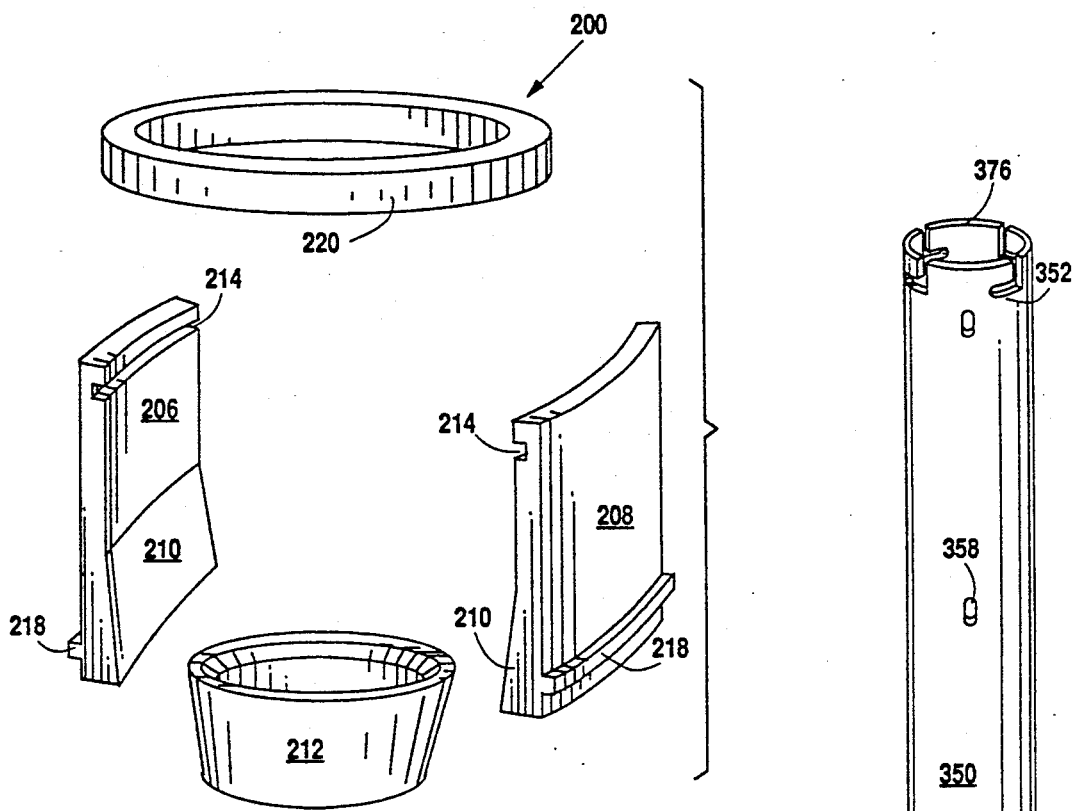
FIG. 6 is a perspective, exploded view of an apparatus constructed in accordance with the present invention for transmitting reactive forces to a strata that are exerted along a line of action at an angle with respect to the strata.

The present invention can best be understood by referring first to FIGS. 1, 6 and 11, in which each of an apparatus for removing material from a hole in a strata, an apparatus for transmitting reactive forces exerted along a line of action at an angle with respect to a load bearing strata to the strata, and an apparatus for aligning and forcing a member through a material is indicated generally at reference numerals 100, 200, and 300, respectively. The apparatus 100 shown in FIG. 1, which may be conveniently referred to as a groover tool, is shown in use for grooving the wall of a hole 110 in a strata 102 in FIG. 2. The apparatus 200, which may be referred to as a collar, is shown in place in a hole 110 in a strata 102 in FIG. 7, and transmits reactive forces to strata 102 regardless of the direction in which they are exerted. The apparatus 300, which may be conveniently referred to as a derrick, is shown in FIG. 11 and in sectional view engaging collar 200 in FIGS. 12A and 12B.

Figure 2:
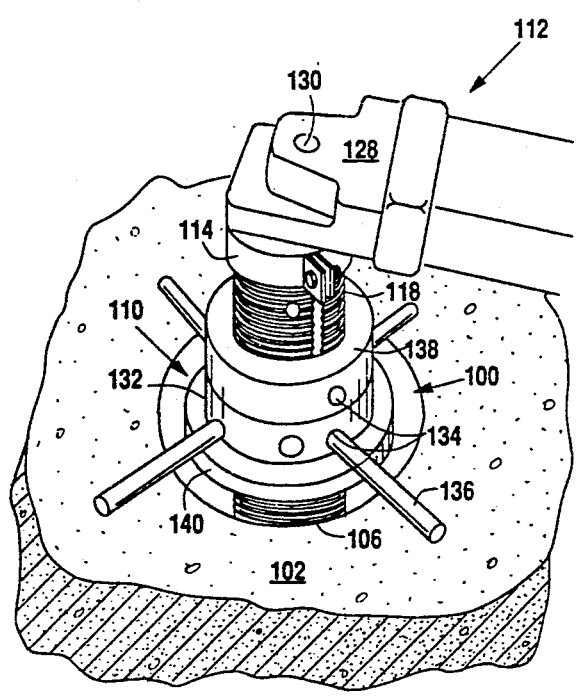
FIG. 2 is a perspective view of the apparatus of FIG. 1 in use for material removal operations and having means for changing the depth of the groove mounted thereto.

Referring first to the groover tool 100 shown in FIGS. 1 and 2, groover tool 100 is comprised of a drive shaft 104 rotatably mounted within an elongate, hollow housing 106 and having a cutting blade 108 mounted on one end thereof for removing material from a surface such as the wall of hole 110 or the surface of a load bearing strata 102 as shown in the alternative embodiment shown in FIG. 4 as will be described. The other end of drive shaft 104 is adapted for engaging power means, indicated generally at reference numeral 112, for rotating drive shaft 104 in housing 106. Power means 112 can be any source of power such as a hand held electrical motor and gear assembly as shown in FIGS. 1 and 2, an electric drill, or other device provided with suitable means for connection to drive shaft 104 as is known in the art. In the presently preferred embodiment of the invention, a band clamp 114, having a screw 116 therein, is provided around the housing 106 for insuring a secure connection between power means 112 and housing 106. A slot 118 is cut longitudinally into a portion of housing 106 to allow the slip fit of housing 106 over the hub 120 of power means 112. Upon proper fit, screw 116 is tightened, tightening clamp 114 around hub 120, and compressing housing 106 to positively engage power means 112. An opening 122 is provided through the wall of housing 106, and drive shaft 104 is provided with a similar hole (not shown) co-incident with opening 122, for receiving a pin (not shown) or other elongate member for selectively preventing rotation of drive shaft 104 relative to housing 106 to facilitate, for instance, the changing of cutting blade 108 when the retaining nut 109 holding blade 108 onto shaft 104 is removed. Cutting blade 108 is a conventional diamond tipped abrasive blade or any other suitable material removal or cutting means as is known in the art.

As will be described below in connection with the description of the use of the groover tool 100, side thrust forces are developed on drive shaft 104 and cutting blade 108. Those side thrust forces are resisted by bearings 124 and 126 at the ends of housing 106.

The gear box 128 is provided with a hole 130 aligned with the axis of drive shaft 104 for receiving and conveying water, compressed air, or other working fluid to cutting blade 108 for cooling the blade and the surface from which material is being removed, lubricating, and reducing the dust and noise produced during removal of the material.

As shown in FIGS. 2–5, groover tool 100 is inserted into the hole 110 in strata 102 to route out material from the inside surface of the hole 110 therein. Groover tool 100 is provided with means for locating the point at which cutting blade 108 is to perform material removal operations mounted on the outside surface of housing 106 in the form of a locating lug 132 having a plurality of spokes 136 extending outwardly therefrom and which is carried by the threads 133 of housing 106. Jam nut 138 is also threaded onto the outside of housing 106 and provides a means for selectively preventing movement of lug 132 with respect to housing 106, thus preventing a change in the depth of cutting blade 108, i.e., by snugging jam nut 138 up against lug 132. Spokes 136 are received within the holes 134 on both lug 132 and jam nut 138 as, for instance, by screw threads, and can be conveniently used as a means for exerting leverage to securely snug jam nut 138 to lug 132 to prevent rotation of lug 132 with respect to housing 106 and to break jam nut 138 apart from lug 132 when it is desired to change the depth at which material removal operations are to be conducted. Spokes 136 extend outwardly from lug 132 a sufficient length to support the housing 106 over the opening of hole 110 in strata 102 as shown in FIG. 2 and to facilitate material removal operations by supporting cutting blade 108 in a plane perpendicular to the surface of hole 110. As will be apparent to those skilled in the art who have the benefit of this disclosure, other means (not shown) can be provided for supporting groover tool 100 over hole 110, for instance, a plate extending outwardly from either lug 132 or jam nut 138. The use of such a plate has the advantage of reducing the amount of dust and debris emerging from hole 110 during material removal operations.

Cutting blade 108 extends down into hole 110 to a location which is controlled by the position of spokes 136 in relation to cutting blade 108. The location can be changed by loosening jam nut 138, rotating lug 132 relative to housing 106, and then snugging jam nut 138 to lug 132. Although cutting blade 108 has been described as extending down into hole 110, it will be understood by those skilled in the art who have the benefit of this disclosure that hole 110 need not necessarily extend downwardly or even exist in a strata such as a concrete slab. Groover tool 100 will function satisfactorily to remove materials if held against the strata 102 in whatever orientation the strata 102 presents, whether strata 102 is horizontal, vertical or overhead, and regardless of the type of strata, e.g., rock, clay, caliche, concrete, and so on, and regardless of whether a concrete slab is present (see, for instance, FIG. 5). In addition, hole 110 need not have an axis which is perpendicular to the surface of strata 102. Nor is removal of materials with groover tool 100 limited to the forming of a groove. Material removal can also be conducted, for instance, on the underside of strata 102 around hole 110 when it is desired to level the bottom surface of a concrete slab to provide a bearing surface for other elements of the invention, as will be described below in connection with the description of FIG. 4.

Removal of material, for instance routing out a groove in the surface of the wall of hole 110, is performed by forcing cutting blade 110 against the surface from which material is to be removed while drive shaft 104 is rotated by power means 112. The groove is extended around the circumference of the wall of hole 110, to the extent it is desired to do so, by sliding groover tool 100 around on the surface of strata 102 on spokes 136 until the outer surface of locating lug 132 encounters the wall of hole 110. To control the depth of the groove in the wall of hole 110, a cutting depth control ring 140 (see FIGS. 2 and 3) of selected thickness is pressed onto the outer surface of locating lug 132 by friction or other fit, for instance, by magnetic attraction. As the thickness of cutting depth control ring is increased (up to the point at which the outer diameter is the same as the diameter of cutting blade 108), the amount of material removed from the inside wall of hole 110 is decreased, e.g., the diameter of discontinuity or depth of groove 216 (see FIG. 12B), is reduced. Controlling the amount of material removed from the surface of hole 110 reduces the time needed for that operation to the maximum extent possible while allowing the lip 218 of collar 200 (see FIG. 12B) to be securely fitted into that discontinuity or groove 216. Further, as will be made clear below, certain advantages of the present invention are enhanced if the amount of material removed is limited. In a presently preferred embodiment, depth control ring 140 is comprised of a resilient and/or slightly elastic material and is provided in a variety of thicknesses for achieving controlled amounts of material removal.

Figure 3:
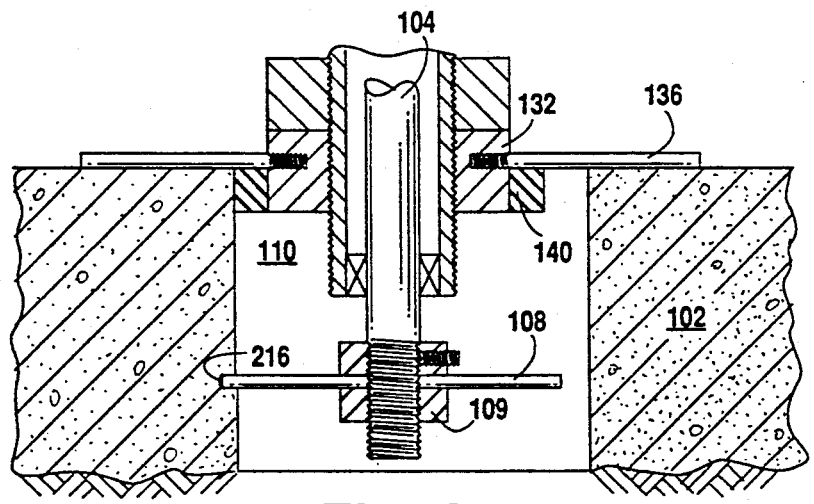
FIG. 3 is a sectional view of the apparatus of FIG. 2.
Figure 4:
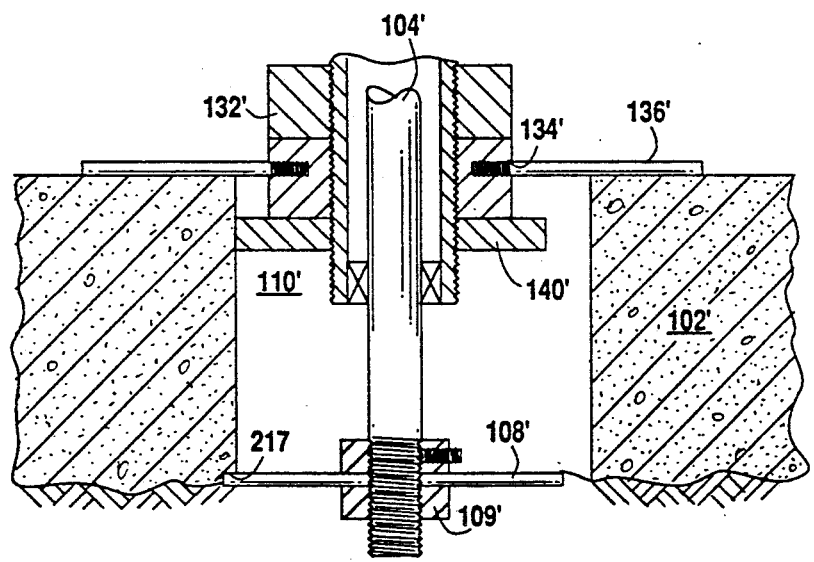
FIG. 4 is a sectional view similar to that of FIG. 3 showing an alternative embodiment for mounting the means for changing the depth of the groove to the apparatus of FIG. 2.
Figure 5:
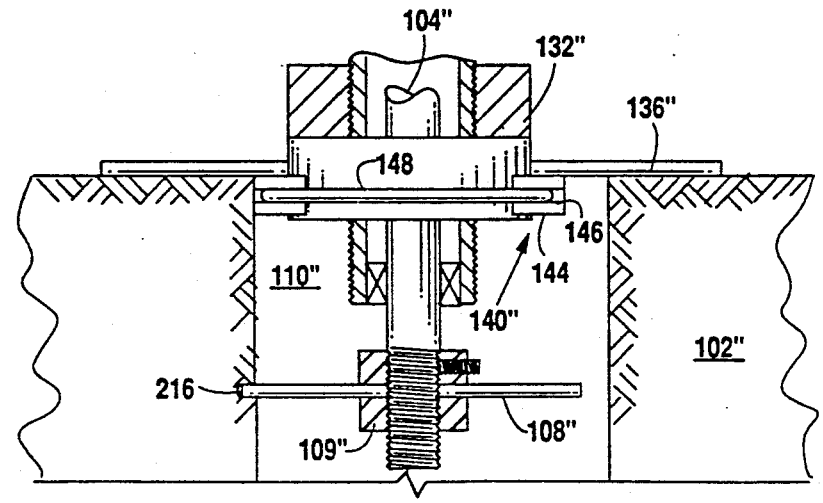
FIG. 5 is a sectional view similar to FIG. 3 showing yet another alternative for mounting the means for changing the depth of the groove to the apparatus of FIG. 2.

Referring to FIGS. 4 and 5, alternative embodiments of the depth control ring shown at reference numeral 140 in FIG. 3 are shown using the same reference numerals and the "prime" designation, where possible, to refer to similar parts. Referring first to FIG. 4, depth control ring 140' is sized to fit snugly against the housing 106' rather than the outside surface of locating lug 132'. In the case of both depth control ring 140 and depth control ring 140', the depth of discontinuity 216 or 216' is achieved by varying the thickness of depth control ring 140 or 140'. Depth control ring 140' is also used in the same manner as jam nut 138, e.g., to prevent rotational movement of lug 132, thereby obviating the need for jam nut 138. Although groover tool 100 is used in any of the embodiments shown in FIGS. 3-5 to level the bottom surface of a strata 102 such as a concrete slab, such a use is illustrated only in FIG. 4. Depth control ring 140' (or 140 or 140" see below) functions in the same manner when the apparatus is used for this purpose; the only difference is that instead of a groove 216 (see below), a flat surface 217 results. Referring to FIG. 5, the depth control ring 140" is comprised of a plurality of semi-circular members, such as those shown at reference numerals 142 and 144, having a longitudinal groove 146 therein. Semi-circular members 142 and 144 are applied to the outside surface of locating lug 132" and held there by means of the extensible member 148 which rests in the groove 146 in members 142 and 144. Extensible member 148 can be an elastic or rubber O-ring or a garter spring. The amount of material removed, e.g., the depth of groove 216" routed out in the wall of hole 110', is controlled by using semi-circular members 142 and 144 of different thicknesses. Semi-circular members 142 and 144 could also be applied to and held on the outside surface of lug 132" magnetically or in other ways known in the art.

Figure 7:
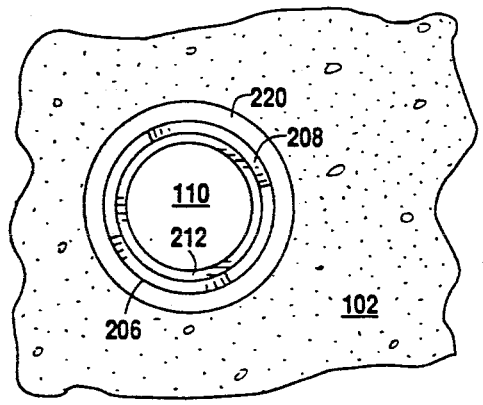
FIG. 7 is a top view of the apparatus of FIG. 6 in a hole in a strata.

Referring now to FIGS. 6 and 7, collar 200, which comprises a means for positively engaging the material, such as strata 102 or soil 204, through which a member is to be forced, will be described in detail. In a presently preferred embodiment, collar 200 is comprised of first and second collar pieces 206 and 208 which are preferably mirror images of each other. The outer surface of each of the first and second collar pieces 206 and 208 is shaped to approximate the shape of the hole 110 in load-bearing strata 102, which is preferably a round hole such as would be drilled through a concrete floor slab or other strata with a conventional diamond core drill (not shown). However, it will be recognized by those skilled in the art who have the benefit of this disclosure that hole 110 need not be round, and collar pieces 206 and 208 need not have rounded outer surfaces, for the collar 200 to function for the intended purpose of resisting the reactive forces which cause movement either away from or down into strata 102 when force is applied thereto. All that is required is that the outer surface of the collar 200 contact the wall of the hole 110 in the strata 102, and generally, the more closely the shape approximates that of the hole 110, the better the ability of collar 200 to transmit forces exerted thereon to strata 102. Each of the first and second collar pieces 206 and 208 is provided with a thickened, or tapered, portion 210, and a tapered bushing 212 is provided for engaging the taper 210 in the first and second collar pieces 206 and 208. When bushing 212 is urged against taper 210, taper 210 causes each of the first and second collar pieces 206 and 208 to tend radially apart from each other. As shown in FIG. 12B, when the bushing 212 engages the tapered portion 210 of the first and second collar pieces 206 and 208 in this manner, the outer surfaces of first and second collar pieces 206 and 208 are expanded outwardly into contact with the wall of the hole 110 in strata 102, thus causing lip 218 to seat securely in groove or discontinuity 216.

Collar 200 is provided with means for engaging an apparatus for exerting force along a line action at an angle with respect to the strata in which the hole is located to force a member through a material, such as the derrick 300 shown in FIGS. 11 and 12, in the form of groove 214 in collar pieces 206 and 208. The outer surface of collar 200 is also provided with means for engaging a discontinuity or groove 216 in the wall of the hole 110 in strata 102 to transmit the force exerted by the force exerting apparatus to which collar 200 is engaged to the strata 102 in which hole 110 is located in the form of a lip 218. As shown in FIGS. 6 and 12B, collar 200 is provided with a retainer ring 220 which restrains radial displacement of the tops of first and second collar pieces 206 and 208 when force is applied thereto. Such restraint is important during certain operations in which extreme forces are applied to collar pieces 206 and 208. Small eccentricities between the means (not shown) for engaging collar pieces 206 and 208 while in place in groove 214 and between lip 218 and groove 216 create a tendency for movement of the tops, or untapered portions, of first and second collar pieces 206 and 208 apart from each other, e.g., radially with respect to the axis of hole 110. That radial movement can cause inward rotation of the tapered portion 210 of collar pieces 206 and 208 such that lip 218 tends to lose contact with groove 216, decreasing the ability of collar 200 to transmit the forces applied thereto to strata 102. Further, that tendency toward radial movement at the top of collar 200 introduces high stresses into strata 102 at the plane of intersection with collar 200. In extreme load cases, those stresses cause strata 102 to spall at that plane unless the tops of first and second collar pieces 206 and 208 are restrained from radial movement by retainer ring 220. Additional resistance to such radial movement is provided by the structure which is apparent in FIG. 12B. Both the lip 218 and tapered portion 210 of first and second collar pieces 206 and 208 are located near the bottom of collar 200 so that, when the tapered bushing 212 engages the tapered portion 210 of collar pieces 206 and 208, not only is lip 218 expanded outwardly into groove 216 as described above, but also tapered bushing 212 is positioned at approximately the same plane as lip 218, e.g., in the same plane as the line of travel of the bottoms of first and second collar pieces 206 and 208 if unrestrained. Tapered bushing 212 resists the inward force and restrains such movement to prevent disengagement of lip 218 from discontinuity 216, thereby preventing any decrease in the ability of collar 200 to transmit reactive forces to strata 102.

Figure 8:
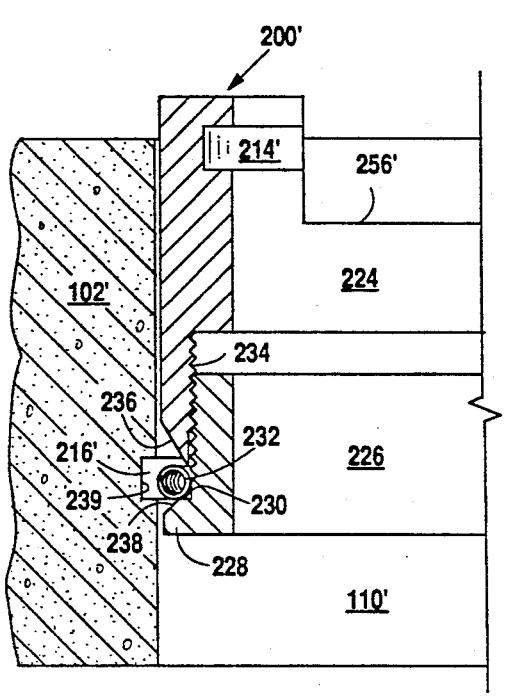
FIG. 8 is a sectional view of an alternative embodiment of the apparatus of FIG. 6 in a hole in a strata.
Figure 10:
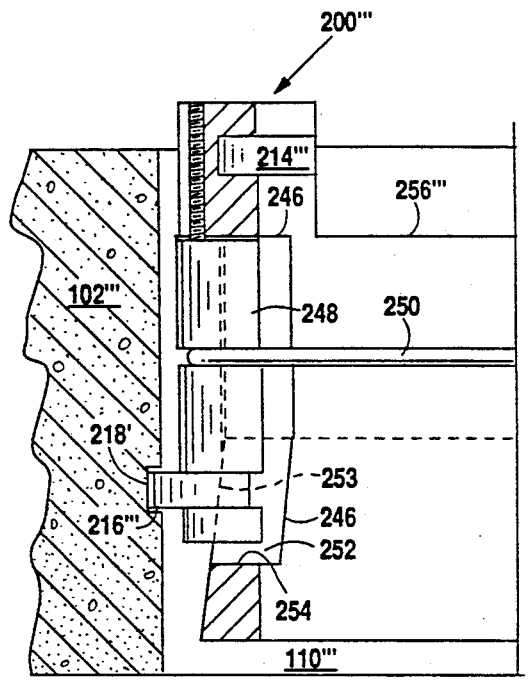
FIG. 10 is a sectional view of another alternative embodiment of the apparatus of FIG. 6 in a hole in a strata.
Figure 9:
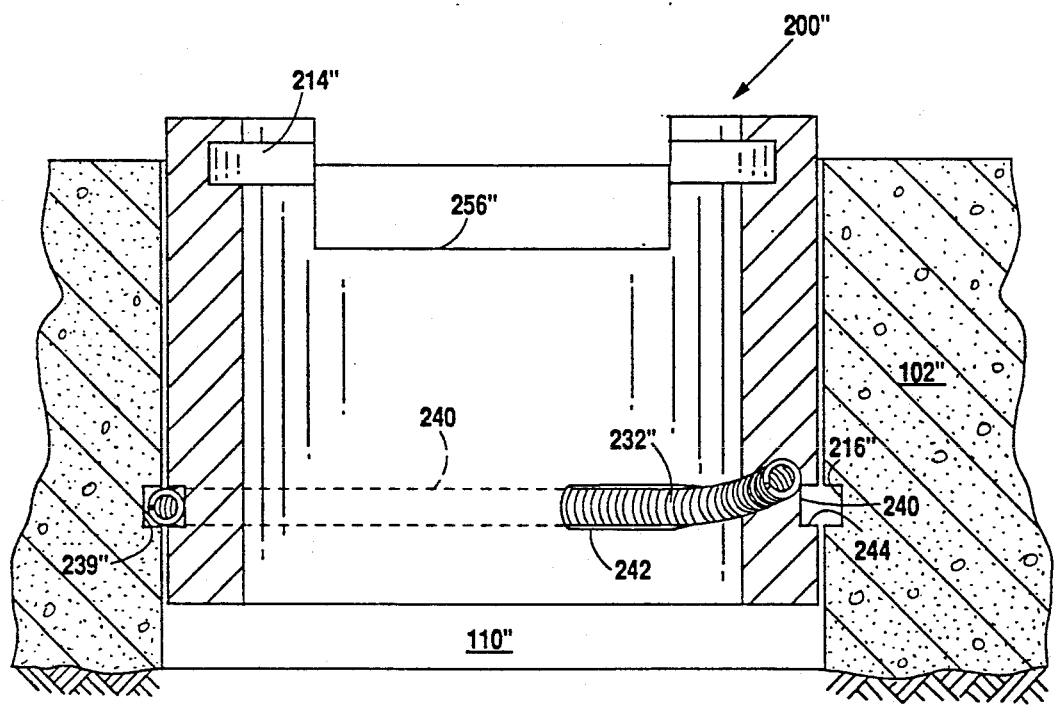
FIG. 9 is a sectional view of another alternative embodiment of the apparatus of FIG. 6 in a hole in a strata.

Referring now to FIGS. 8-10, alternative embodiments of the apparatus for transmitting force to strata 102 are shown. Referring first to FIG. 8, collar 200' is comprised of upper and lower threaded members 224 and 226, respectively. Lower threaded member 226 is provided with a flange 228 having a shoulder 230 on the upper surface thereof for engaging a radially extensible, flexible member 232. Radially extensible member 232 is shown in FIGS. 8-10 as a garter spring, but it will be understood by those skilled in the art who have the benefit of this disclosure that radially extensible member 232 may be either continuous or severed and can be constructed of any material and in any shape so as to expand radially either as a result of the springiness of the material comprising the member 232 or by cooperation between member 232 and the other parts of collar 200 as described below. For instance, radially extensible member 232 can take the form of a cut ring or "O-ring" (not shown) or any other member which when placed in position, closely approximates the outer circumference of lower threaded member 226 until upper threaded member 224 is advanced downwardly, such as by screwing on threads 234, such that the beveled surface 236 at the lower edge thereof engages radially extensible member 232, and expands member 232 outwardly into engagement with groove 216'. As will be explained, collar 200', like collar 200 and the alternative embodiments shown in FIGS. 9 and 10, transmits forces exerted thereon to the strata 102 by engagement of groove 216 or 216'. To further ensure engagement of the groove 216' by radially extensible member 232 upon application of upward force on collar 200', the shoulder 230 of flange 228 is provided with a beveled surface 238 which engages member 232 and, by wedging action, forces member 232 into groove 216'. If radially extensible member 232 takes the form of a garter spring such as the garter spring shown in FIG. 9, the circular outside surface of member 232 likewise provides a beveled surface which, when engaged by shoulder 230, causes the member 232 to be expanded outwardly into the groove 216'. Depending upon the amount of material removed from the wall of hole 110, the outer surface of radially extensible member 232 engages the bottom 239 of groove 216', preventing further outward movement. Hence, it can be seen that the depth control ring 140 of groover tool 100 (see FIGS. 2 and 3) cooperates with radially extensible member 232 to help determine the amount of force which can be transmitted to load-bearing strata 102. If too much material is removed from groove 216' by the cutting blade 108, member 232 could expand radially out of engagement with shoulder 230 when shoulder 230 moves upwardly or downwardly with respect to groove 216'.

The radial extensibility and flexural characteristics of member 232 are used to advantage in the apparatus shown in FIG. 9 in which the parts corresponding to the parts of the apparatus previously described are referred to with the "double prime" designation. For instance, collar 200" is provided with a groove 240 in the outer surface thereof communicating through an opening 242 in the wall of collar 200" into the hole 110". A severed extensible member 232" is threaded through opening 242 into slot 240 once collar 200" has been placed into the hole 110" in strata 102". Severed extensible member 232" is channeled via opening 242 around the outer surface of collar 200" and resides in the space formed by the groove 240 in collar 200" and the groove 216" in strata 102". When force is exerted upon collar 200", the surfaces 244 of groove 240 engage the outer surface of extensible member 232" to prevent movement of collar 200", thereby effectively transmitting the force exerted thereon to strata 102". Again, depth control ring 140 cooperates with extensible member 232" to determine the amount of force which can be transmitted. If groove 216" is too deep, member 232" will tend so deeply into the groove 216 that collar 200" will be able to move within the hole 110" in strata 102".

Referring now to FIG. 10, a third alternative embodiment of the apparatus for transmitting reactive forces to a strata 102 is shown in partial sectional view. Collar 200''' is provided with a recess 246 in the outer surface thereof for receiving a split collar 248 therein. An O-ring, garter spring, or other extensible member 250 is provided to apply a light, radially inward force to prevent the split collar 248 from moving away from the recess 246. Magnetic forces could likewise be utilized for that same purpose. The bottom of collar 200''' is provided with a tapered portion 252, the slant of which mates with a slanted surface 253 on the inside surface of the split collars 248. When force is exerted on collar 200''', collar 200''' moves vertically in hole 110''', causing the taper 252 of collar 200''' to expand split collar pieces 248 apart from each other such that the lip 218''' on the outside surface thereof is biased toward the groove 216''' in the wall of hole 110'''. A shoulder 254 is provided at the bottom of the tapered portion 252 of collar 200''' to limit the upward movement of collar 200''' relative to split collars 248 by contact with the bottom of split collars 248. Collar 200''' is also provided with a screw 258 to allow advancement and positioning of split collar pieces 248 relative to collar 200''' along taper 252 and to positively engage the top of split collar piece 248 to prevent relative movement of split collar piece 248 upwardly. Such movement would occur when force is exerted on collar 200''' tending to push collar 200''' further down into hole 110''', and screw 258 provides for the transmission of force into strata 102 regardless of whether the force is exerted upwardly or downwardly.

The mechanism for transmitting a force into load bearing strata 102 with collar 200 (it will be recognized that, when reference is made to collar 200, reference is also made to collar 200', 200'', and 200''', as is the case with all of the referenced parts of those collars) is that of introducing an interference to carry shear forces between the wall of the hole 110 and collar 200. Such interference can be in the form of lips 218 and/or extensible members 232 as described above, which can be placed in groove 216 or other type of discontinuity (such as the groove 240 in collar 200'') to cause "lock up" to be achieved. Those skilled in the art who have the benefit of this disclosure will recognize that further variations would likewise introduce such an interference between collar 200 and strata 102. For instance, ball bearing elements (not shown) could be introduced into the track formed by groove 240 and groove 216'' in place of extensible member 232, as could an epoxy or other substance that would harden in place. The interference could likewise be created by ridges, threads or other surface irregularities on the outside surface of collar 200 or inside surface of hole 110, or by gluing collar 200 to hole 110 with a suitable chemical bonding agent.

By way of further example, radially extensible member 232'' (see FIG. 9) need not be introduced from opening 242 in the interior portion of collar 200''. Instead, a severed or non-severed member 232'' can simply be compressed in groove 240 flush with the outer surface of collar 200'', for instance, with hand pressure, while collar 200'' is inserted into hole 110''. When collar 200'' is inserted into the hole 110'' in load bearing strata 102, extensible member 232'' is held flush with the outer surface of collar 200'' by the wall of hole 110'' until groove 240 and groove 216'' are aligned. Once groove 240 and groove 216'' are aligned, radial expansion of member 232'' into groove 216'' creates such an interference and "lock-up" is achieved.

Figure 6A:
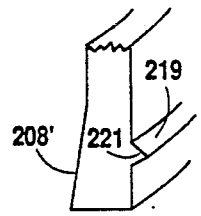
FIG. 6A and 6B are perspective views of a portion of two different alternative embodiments of the apparatus of FIG. 6.

Similarly, such interference can also be achieved by using a lip having a substantially triangular cross-section such as the lip 219 shown in FIG. 6A in place of the lip 218 having a more or less square configuration such as that shown in FIGS. 6 and 12. First and second collar pieces 206' and 208', each having a pointed lip 219, are set in place in a hole 110 and tapered bushing 212 is then pounded into engagement with the tapered portions 210 thereof. The outward expansion resulting from the relative movement of tapered bushing 212 and tapered portions 210 of first and second collar pieces 206' and 208' as described above causes the pointed lip 219 to "bite" into the wall of hole 110, effectively forming a groove 216, to create the discontinuity required for lock-up.

In materials which are loosely packed such as soil, the necessary interference can be obtained from a single piece collar 200 having an auger or screw blade (not shown) formed on the outside surface thereof instead of the lip 218, and no groove or discontinuity 216 need be prepared. Such a collar is screwed into the material by equipping derrick 300 with a motor such as the motor described below for rotating a string of force transmitting members to drill through hard formations by mounting such a reactive force transmitting member on the end of the string by means of an adapter such as the adapter ring 384 described below. The ability of such a collar to resist movement along the longitudinal axis of the hole therethrough is directly dependent on the surface area of the blade or screw. Such structure can even be used successfully to transmit reactive forces to such loosely packed materials as sandy soil or loam by using a longitudinally extended reactive force transmitting apparatus with radially extending wings projecting therefrom that is impacted or forced into the material through which the member is to be forced.

Figure 6B:
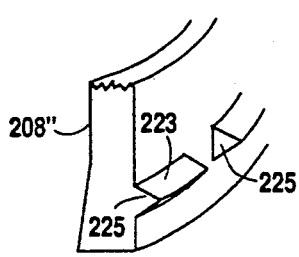

When a derrick 300 is equipped with a motor for rotating a string of force transmitting members such as the push rods 346 or 350 having a bit mounted thereto to drill through hard formations as described below, collar 200 must not only transmit the reactive forces of hydraulic cylinder 326 to strata 102 but must also resist or transfer counter-rotational force. Such resistance is achieved by one or more pointed projections or keys (not shown) extending radially outwardly from the outside surface of first and second collar pieces 206 and 208. Such projections are preferably located at the bottom of collar pieces 206 and 208 so that when tapered bushing 212 is forced or pounded down between the collar pieces 206 and 208, the engagement of the tapered portions 210 by bushing 212 causes those projections to be forced into strata 102. Further, any tendency of such projections to back out of strata 102 is countered by their location in substantially the same plane as bushing 212, which resists inward movement of the portion of the collar piece 206 and 208 located in that plane. The split collar pieces 248 of collar 200''' can likewise be provided with such projections. Referring to FIG. 6A, the collar piece 208' resists rotational movement by engagement of the end surface 221 of lip 219 with the strata 102, the lip 219 having penetrated into strata 102. As shown in FIG. 6B, resistance can also be achieved by using a collar piece 208'' having a discontinuous lip 223, the end surfaces 225 of which engage strata 102.

The single piece collars 200'', as well as the two-piece collar 200', shown in FIGS. 8, 9, and 10, are characterized by certain advantages which make them the embodiments of choice in certain applications. For instance, their round configuration makes them particularly resistant to the rotational movement discussed above which necessitates the use of retainer ring 220 with collar 200 to decrease the likelihood of spalling of strata 102. Further, inasmuch as those collars include fewer parts than collar 200, they can be simpler to use. However, because collar 200, being comprised of first and second collar pieces 206 and 208, is less dependent on closely corresponding circumferential dimensions between the wall of hole 110 and the other surface thereof than collars 200', 200" and 200'", collar 200 is the embodiment of choice for holes which may not be exactly circular or when the collar 200 must be re-used and there may be slight variations in the diameter of several holes 110.

Referring now to FIGS. 6, 8, 9, and 10, groove 214 is located in the upper portions of the respective collars 200. In the case of the collars 200', 200" and 200'", which are all of single piece construction (as opposed to the split construction of collar 200), the top margin of each is castellated, i.e., is provided with cut-outs of portions of the top margin, shown generally at reference numerals 256', 256", and 256'", respectively. The function of these cut-outs 256', 256", and 256'" will be made clear below.

Referring now to FIGS. 11 and 12, there is shown a presently preferred embodiment of an apparatus for selecting the line of action along which a member is to be forced through soil or other materials. That line of action selecting means is, for convenience, referred to as a derrick, and is indicated generally at reference numeral 300. Derrick 300 comprises a plurality of legs 302, having cams 303 pivotally mounted thereto for a purpose which will be made clear below, and upper 304 and lower 306 plates slidably mounted to the legs 302. Although the terms "upper" and "lower" have been used with regard to the description of the plates 304 and 306, it will be understood by those skilled in the art who have the benefit of this disclosure that derrick 300 need not be used in a position or orientation such that plates 304 and 306 are always "upper" and "lower". Derrick 300 can be used in any orientation, for instance on a slanted surface, vertical surface, or even "upside down". Consequently, the plates 304 and 306 may best be referred to as first and second plates, respectively, or even generically as plates 304 and 306.

For the same reason that plates 304 and 306 are not referred to as being "upper" and "lower" plates, derrick 300 is referred to as a means for selecting a line of action along which a member is to be forced. In other words, when positioned on a concrete slab, activation of hydraulic cylinder 326 results in a line of action which is exerted at substantially a right angle to that concrete slab. There is no requirement that the line of action be exerted at a right angle, however. Derrick 300 can be positioned on a platform (not shown) with an inclined surface or two of the legs 302 can simply be shorter than the other legs 302 such that the line of action is slanted with respect to the horizontal. Hence, the present specification refers to the line of action being exerted at an angle with respect to the strata, it being recognized that the angle could be a ninety degree angle or, for instance, a seventy degree angle such as might be used to place a soil anchor for a guy wire.

Means is provided for releasably securing plates 304 and 306 at a selected location along the legs 302 of derrick 300 in the form of the holes 308 spaced along the length of legs 302, the pins 310 slidably received within holes 308, and the holes (not numbered) in the blocks 312 which are attached to or integral with plates 304 and 306. The holes 312 could also be located in plates 304 and 306 such that blocks 312 are unnecessary.

Figure 13:
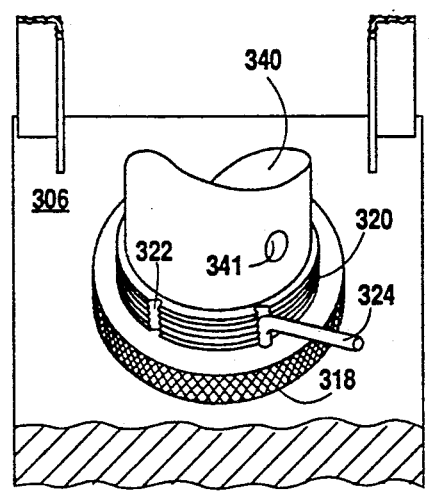
FIG. 13 is a perspective view of a portion of the apparatus of FIG. 11.

Means is mounted to derrick 300 for engaging a material engaging means such as a collar 200 positioned in a hole 110 to transmit reactive forces resulting from the resistance of the material, such as soil 204, to the forcing of a member into the material in the form of locking dog 314 extending through a hole (not numbered) in plate 306. As shown in more detail in FIGS. 12B and 13, locking dog 314 is a tubular member through which the member passes when the member forcing means, e.g., hydraulic cylinder 326, is activated and is provided with means on one end thereof for releasably engaging the groove 214 in collar 200 by rotation with respect thereto in the form of the ears 316 which are integral with and extend outwardly from the outer surface of the bottom edge of locking dog 314 around a portion of the circumference thereof. The other end of locking dog 314 is provided with means for engaging derrick 300 in the form of nut 318 which is carried on the threads 320 cut into locking dog 314. Rotation of nut 318 relative to locking dog 314 causes axial movement of locking dog 314 relative to nut 318 because nut 318 rests on plate 306. A similar nut 319 is also carried on threads 320, but is positioned on the other side of plate 306 for a purpose which will be made clear below. Nut 318 is used both to lower the ears 316 into alignment with groove 214 and, once locking dog 314 has been rotated to slide ears 316 into groove 214, to move locking dog 314 upwardly into engagement with the upper surface of groove 214, thereby snugging up the connection of derrick 300 to collar 200 in load bearing strata 102.

As noted above, the first and second collar pieces 206 and 208 of collar 200 are preferably mirror images of each other and, when placed in hole 110, occupy only a portion of the circumference of the hole 110. In a presently preferred embodiment, each of the first and second collar pieces 206 and 208 occupies an arc of approximately 80° to 90° of the entire circumference of hole 110, and first and second collar pieces 206 and 208 are placed in hole 110 opposite each other, i.e., so that their center points are about 180° apart. The gap (not numbered) between collar pieces 206 and 208 allows the ears 316 of locking dog 314 to be positioned between first and second collar pieces 206 and 208 on the same level as the groove 214, and locking dog 314 is then rotated approximately 90° to releasably lock locking dog 314 to collar 200. As noted above, each of the collars 200'", 200", and 200'", shown in FIGS. 8, 9, and 10 is castellated, e.g., provided with cut-outs 256', 256", and 256'", respectively, which allows the ears 316 of locking dog 314 to be positioned below the top margin of each of the respective collars 200', 200", and 200'" and aligned with each of the respective grooves 214', 214", and 214'". The outer diameter and vertical dimension of ears 316 are slightly smaller than the diameter of the bottom and vertical dimension of the groove 214', 214", and 214'", thereby allowing locking dog 314 to be rotated relative to collar 200', 200", and 200'" so that ears 316 engage groove 214', 214", or 214'", as the case may be, to prevent relative axial movement with respect thereto. It will be apparent to those skilled in the art who have the benefit of this disclosure that locking dog 314 could also be provided with threads (not shown) on the outer surface at the lower end thereof for engaging a matching set of threads (not shown) on the inside surface at the top of a collar 200, nut 318 effectively functioning as a lock or jam nut, or that the diameter of hole 110 could be sized such that the threads on the outside surface of locking dog 314 could themselves serve as a means for transmitting reactive forces to the strata 102 by cutting into the wall of hole 110.

Locking dog 314 and nut 318 are provided with a plurality of slots 322 for receiving a locking pin 324 for preventing rotational movement of nut 318 with respect to locking dog 314, thereby maintaining the snug engagement of strata 102 by locking dog 314. Additionally, insertion of locking pin 324 into one of the slots 322 allows the locking dog 314 and nut 318 to be rotated together on plate 306 without changing that snug engagement.

Referring to FIGS. 11 and 12A, means for forcing a member or device through the material such as soil 204 is mounted on the plate 304 in the form of a double acting hydraulic cylinder 326. It will be understood by those skilled in the art who have the benefit of this disclosure that hydraulic cylinder 326 is but one means of providing the force necessary to move such a member through such materials and that other means could also provide the necessary force. Hydraulic cylinder 326 includes a ram 328 (see FIG. 12A) which passes through a hole 330 in first plate 304 and which is proided with means for releasably mounting a member or device thereto in the form of an end piece 332 mounted on the end thereof, for instance, on threads 333.

End piece 332 is provided with a slot 334 in one end thereof for receiving a locking pin 336 therethrough and multiple shoulders 338 and tapered planes 342 for engaging, aligning and seating a member or device, such as a force transmitting member or sample tube 340 when forced into the material such as soil 204, the nose 343 of end piece 332 being received within the interior diameter of the end of such members. The force transmitting members may take the form of push rods, two different embodiments of which are shown at reference numerals 346 (FIGS. 12 and 17) and 350 (FIGS. 11 and 14), both of which are included in the more generic term "member" which can be mounted to end piece 332. As end piece 332 is advanced against, for instance, push rod 350 (see FIG. 11), the upper margin of push rod 350 rides upon the tapered portion 342 of end piece 332, the incline of taper 342 causing lateral displacement of push rod 350 until the axis of push rod 350 is aligned with the axis of end piece 332. Alignment is further ensured by, and end piece 332 is capable of being used with members of different diameters because of, the plurality of tapers 342 and 342' and shoulders 338 and 338'.

As shown in FIG. 12A, end piece 332 is provided with an elongate slot 334 for receiving locking pin 336 therethrough to connect a force transmitting or other member thereto. Because the diameter of the nose 343 of end piece 332 is less than the internal diameter of the members such as push rods 346 or 350, or sample tube 340, the member can more and swing laterally from side-to-side as well as pivot on the axis of locking pin 336. Further, when the member forcing means, e.g., hydraulic cylinder 326, is activated, the elongate nature of slot 334 allows locking pin 336 to move vertically in slot 334 so that shoulder 338 bears against the upper margin of the member mounted thereto, thereby relieving the load on pin 336. The amount of lateral movement is controlled by the difference in the diameters of nose 343 of end piece 332, the extent of which the nose 343 extends into the member pinned thereto, and the internal diameter of the member pinned thereto. Lateral, swinging movement of the member pinned to end piece 332 greatly facilitates installation or removal of the member as well as other operations in which the member blocks access to the hole 110.

The force transmitting member can take several forms, one of which is a telescoping push rod 346 (FIGS. 12 and 17) made of several sections, three such sections being shown at reference numerals 349', 349" and 349''', each section 349 being provided with openings 348 spaced along the length thereof. A pin (not shown) is provided for placement in a selected opening of section 349' which is aligned with the openings 348 of the next smaller sections 349" and 349''' to hold the telescopic push rod 346 in the fully or partially extended or non-telescoped position. The telescoping ability of push rod 346 provides the ability to advance and/or retract a member mounted on the end thereof in a manner not limited by the length of the stroke of hydraulic cylinder 326. Likewise, the selective positioning of plate 304 to which the hydraulic cylinder 326 is mounted allows push rod 346 of a given length to be advanced or retracted by greater lengths than could be achieved if plate 304 were fixed along derrick legs 302.

Figure 17:
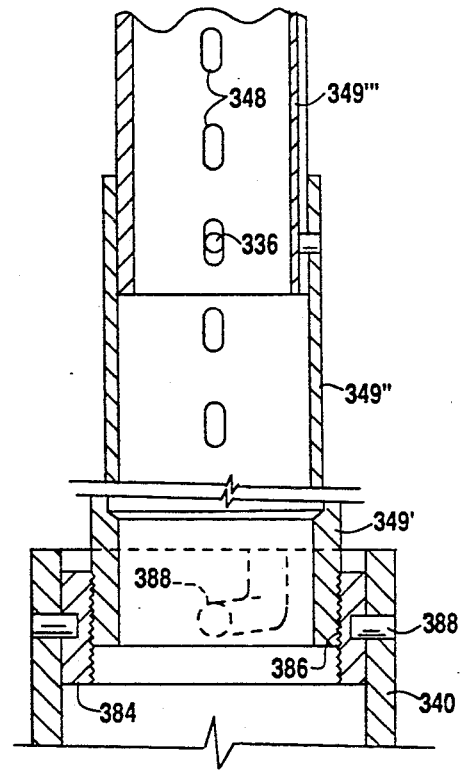
FIG. 17 is a longitudinal sectional, partially exploded view of a telescoping push rod for use with the apparatus of FIG. 11, having an adapter ring mounted thereto for engaging a member or device.

As shown in FIG. 17, each of the sections 349', 349" and 349''' of push rod 346 is provided with a longitudinal slot 380 having a pin or key 382 from the next larger telescoping section 349" or 349''' positioned therein to prevent rotational movement of each section 349 relative to the other sections 349. In that manner, the openings 348 in each section are kept in radial alignment, thereby facilitating insertion of the locking pin 347 in the desired opening 348 along the length of push rod 346. The openings 348 are vertically elongated to obviate the necessity for exact coincidence of the openings 348 of each section 349', 349" and 349''' before lock pin 347 can be inserted therethrough.

Section 349' (or push rod 350, not shown in FIGS. 12 and 17) is provided with an adapter ring 384 which is threadably received on the threads 386, or otherwise mounted, on section 349'. Adapter ring 384 is provided with radially extending pins 388 for engaging the J-slots 364 of a cylindrical member such as sample tube 340 as will be described. Adapter ring 384 also provides a convenient means for attaching other members (not shown), including, but not limited to, well casings, well points, benchmarks, soil anchors, penetrometers, piezometer tubes, soil gas samplers, stepped blade soil pressure transducers, or geophysical logging equipment, to push rods 346 or 350, and can be supplied in different sizes or having stepped threads for mounting members having different diameters to push rods 346 or 350. Such members can, of course, be mounted directly to the end of a push rod 346 or 350 as well.

Figure 14:
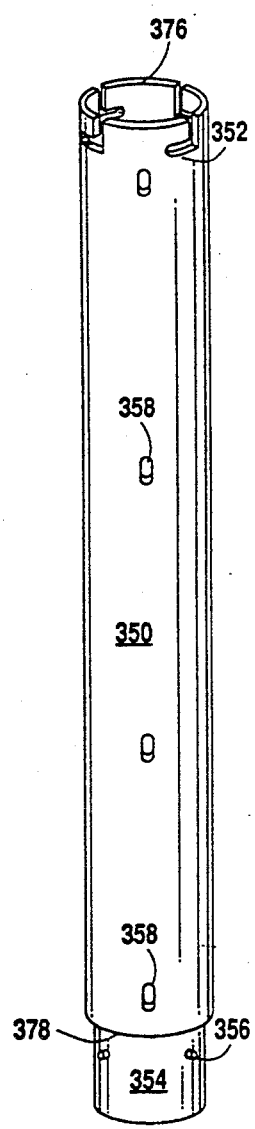
FIG. 14 is a perspective view of an alternative embodiment of a force transmitting means for mounting on the apparatus of FIG. 11.

An alternative embodiment of a force transmitting member for use in connection with the apparatus of the present invention and having a bayonet-type locking capability is shown at reference numeral 350 in FIGS. 11 and 14. Push rod 350 can be mounted to end piece 332 using the same locking pin 336 and the openings 358 therein as used for push rod 346. The push rod 350 is provided at one end with four J-slots 352 having a slight taper in the bottom portion of the "J." The other end of push rod 350 is provided with a portion 354 of slightly reduced diameter, the outside surface of the portion 354 being provided with four radially extending pins 356. The end of the push rod 350 having the J-slots 352 located therein is mated to the reduced diameter portion 354 of an adjoining push rod 350, the pins 356 are aligned with the J-slots 352, and the adjacent push rod (not shown) turned to snug the two push rods 350 to each other as a result of the taper in the J-slots 352. The taper in J-slots 352 insures that when the reduced diameter portion 354 of push rod 350 is advanced into the larger diameter end 376 of an adjacent push rod 350, the shoulder 378 positively and securely engages the end 376 of the adjacent push rod 350 until rotational movement is used to unlock adjacent members. Engagement of the adjacent push rod 350 in this fashion increases the ability of each push rod 350 to efficiently transfer the force exerted by hydraulic cylinder 326 to the adjacent push rod 350, prevents excessive loading of pins 356, and securely connects and aligns the push rods 350 to each other.

As noted above, each push rod 346 or 350, as well as sample tube 340, is provided with the openings 348, 358 and 341, respectively, through which a pin (not shown) such as the pins 310 or the anti-drop washer 370 described below can be inserted to prevent push rods 346 or 350 or sample tube 340 from falling into the void created in the material under hole 110 or to provide a convenient point at which those members can be rotated to lock or unlock them from each other. The elongate member or anti-drop washer 370 prevents downward movement of those members by bearing against the top margin of locking dog 314 when sample tube 340 or push rods 346 or 350 extend downwardly therethrough.

Figure 15:
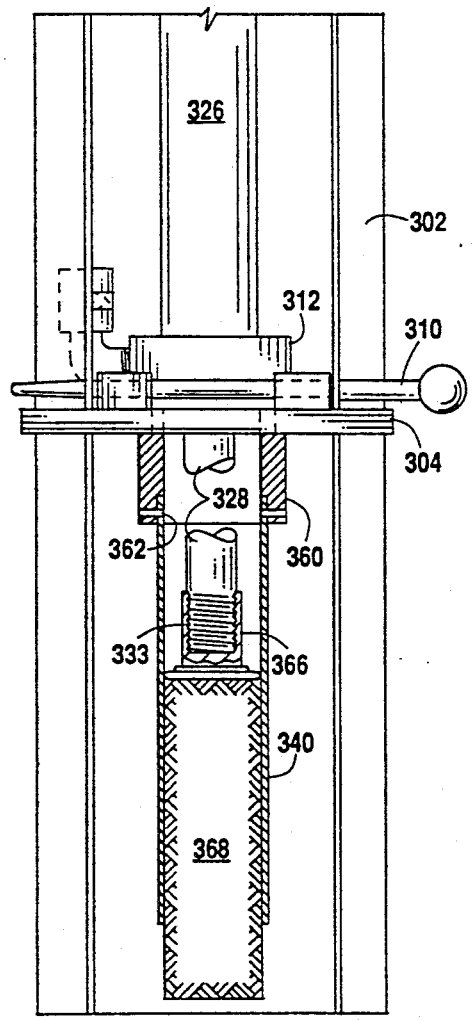
FIG. 15 is a sectional view of a portion of the apparatus of FIG. 11 in use for extruding a sample from a sample tube mounted thereto.

As shown in FIGS. 12A and 15, the hole 330 in upper plate 304 is threaded for receiving the threaded end of extruder head 360. Extruder head 360 is provided with means for releasably mounting a member such as a sample tube 340 to prevent movement of the member when hydraulic cylinder 326 is activated in the form of four pins 362 extending inwardly for receiving the J-slots 364 in the top of sample tube 340 (FIG. 12B). Sample tube 340 is secured to extruder head 360 by removing any push rods 346 or 350 which may be pinned to end piece 332, aligning pins 362 with J-slots 364, inserting the top of the sample tube 340 into extruder head 360, and rotating sample tube 340 with respect to extruder head 360, the taper in the bottom of the J-slots 364 causing sample tube 340 to move upwardly to seat against the shoulder 361 of extruder head 360. When plunger 366 is screwed onto the threads 333 on the end of the ram 328 of hydraulic cylinder 326 (shown in FIG. 15) and hydraulic cylinder 326 is activated, the sample plug 368 is extruded from sample tube 340.

Although hydraulic cylinder 326 is capable of considerable force when activated to force a member through a material such as the soil 204 even when the material is hard, i.e., high clay content, rock, etc., there are certain formations that cannot be breached without drilling. The structure of derrick 300 is adaptable for drilling through such formations. The ram 328 of hydraulic cylinder 326 turns freely within hydraulic cylinder 326 such that all that is necessary to impart rotational motion to a string of force transmitting members such as push rods 346 or 350 is a motor, which can be hydraulic powered by the same hydraulic fluid which powers hydraulic cylinder 326, and teeth or other means for translating the rotational motion of such a motor to the string such as is well known in the art. Likewise, a suitable thrust bearing, mounted between end piece 332 and the force transmitting members, allows rotation of the force transmitting members while at the same time transmitting the thrust forces developed by hydraulic cylinder 326. The member mounted on the end of the string would, of course, be a drill bit of the appropriate size, mounted by an adapter ring such as adapter ring 384 having a coupling mechanism resistant to rotational movement in the direction of rotation of the bit as is also well known in the art.

As has been described, it is often advantageous to disconnect sample tube 340, push rods 346 and 350, or any other member mounted to end piece 332, from end piece 332, from end piece 332 while preventing vertical movement with respect to the other components of derrick 300 such as locking dog 314. Disconnecting those members is especially advantageous in operations such as those which are described below that create a bore from which the sample tube 340 or push rod 346 or 350 is extracted during operations. In such an operation, for instance a material sampling operation, progressive shortening of the string of push rods 346 or 350 to retrieve the soil sample necessitates that the push rods 346 or 350 be released or disengaged with respect to each other or released or disengaged from end piece 332 from time to time. Disconnecting those cylindrical members creates the possibility that the string can fall "down the hole." To prevent loss of the string downhole, an elongate member similar to pin 310 is inserted through one of openings 348 or 358 through the wall of one of the push rods 346 or 350, the ends of pin 310 resting on the top of locking dog 314, thereby preventing downward movement of the entire string.

Figure 16:
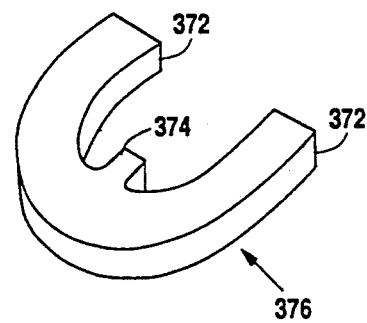
FIG. 16 is a perspective view of an anti-drop washer for use in practicing the method of the present invention.

Referring to FIG. 16, there is shown another means of preventing such downward movement relative to locking dog 314 in the form of an anti-drop washer 370, the inside surface of which is shaped to approximate the surface contour of a member which is cylindrical, i.e., sample tube 340 or push rods 346 or 350. The two ears 372 of washer 370 fit fairly closely around the outer surface of such cylindrical members. At a location along the inside surface of ears 372, a tang 374 is provided for projecting into any one of the holes 341 in sample tube 340, or the holes 348 or 358 in push rods 346 or 356 when the ends 372 of anti-drop washer 370 encircle the sample tube 340, or the push rod 346 or 356. When, for instance, sample tube 340 is in the position shown in FIG. 13, the tang 374 of anti-drop washer 370 (not shown in FIG. 13) is inserted into hole 341 and anti-drop washer 370 rests on top of locking dog 314 to prevent vertical movement of sample tube 340 with respect to locking dog 314.

As will be apparent from the foregoing description, a member mounted on end piece 332 can be forced deeper into a material such as the soil 204 by extending the string of force transmitting members to which the member, such as sample tube 340, is mounted. However, those skilled in the art will recognize that, as the string is extended, the weight of the string increases, increasing the difficulty of handling the string. Consequently, one of the uses of a pin such as locking pin 310 and holes 341, 348 and 358 is for handling the string. For instance, when pin 310 extends through holes 348 in the uppermost push rod 346 or 350 and the uppermost push rod 346 or 350 is detected from end piece 332, the entire string can be rotated manually by grasping pin 310 and exerting force thereon to rotate the string until the J-slots 352 are aligned with the pins 356 on a push rod 346 or 350 which has just been mounted on end piece 332 or until the holes 348 therein are aligned with the slot 334 in end piece 332 for receiving lock pin 336, as the case may be. Further, rotation of the string is also used to advantage to place a well casing, well point, benchmark, soil anchor, or other member or device in the soil 204 or other material. Such members are mounted to an adapter ring 384 or to the end of the force transmitting member such that all that is required to disconnect such members from adapter ring 384 or the force transmitting member to leave such members in the material 204 is relative counter-rotational movement such as can be achieved using one of the pins 310 in this manner.

With reference to the preceding detailed description of the presently preferred embodiments of the invention, the method of the present invention will now be described with particular reference to obtaining a soil sample and extruding that sample on-site. As set out above, a hole 110 is first drilled through strata 102 and, referring to FIGS. 2 and 3, a discontinuity or groove 216 is routed out in the wall of the hole 110 in strata 102. Although strata 102 and soil 204 are shown in FIG. 12 as separate facies, i.e., a concrete slab poured over soil, it will be understood by those skilled in the art who have the benefit of this disclosure that the operation of the apparatus of the present invention and methods described herein do not require such sites. Strata 102 could be a natural formation of rock, a layer of asphalt, clay or caliche, or even tightly compacted soil such that the material which is to be sampled is itself the load bearing strata 102. Hence, there is no line of demarcation between facies shown in FIGS. 3-5 and 8-10.

The point at which material is to be removed from the wall of hole 110 to form discontinuity or groove 216 is selected by loosening the jam nut 138 on the housing 106 of groover tool 100, rotating the locating lug 132 to the desired location on the threads of housing 106, and then snugging jam nut 138 up against locating lug nut 132 to prevent subsequent rotational movement of locating lug 132 relative to housing 106. The depth of the groove 216 in the wall of hole 202 is then selected by press fitting a depth control ring 140 of the appropriate thickness around the outer circumference of locating lug 132.

Collar 200 is positively engaged to the material through which the member is to be forced by placing the first and second collar pieces 206 and 208 into hole 110 and wedging the tapered bushing 212 between first and second collar pieces 206 and 208. The lip 218 on the outside surface of the first and second collar pieces 206 and 208 is urged outwardly into the groove 216 by the tapered bushing 212 bearing against the tapered portion 210 of first and second collar pieces 206 and 208, and retaining ring 220 is placed around the collar pieces 206 and 208 as shown in FIG. 7. Positive engagement of strata 102 (or any material) in that fashion prevents axial movement of collar 200 in hole 110 regardless of the direction of the reactive forces applied thereto.

The collar 200 in hole 110 is then engaged by the ears 316 of locking dog 314 by placing derrick 300 over the hole 110, lowering locking dog 314 to the desired height by turning the nut 318 carried on threads 320 until ears 316 are aligned with the groove 214 in collar pieces 206 and 208. Nut 318 and locking dog 314 are releasably locked to keep ears 316 at that height using the locking pin 324, and then the entire locking dog 314, nut 318 and locking pin 324 is rotated approximately 90° to engage the groove 214 at the top of collar 200, thereby resisting relative vertical movement. If it is desired to snug derrick up to strata 102 as described above to reduce "play" in the system, locking dog 314 is grasped to prevent rotation, locking pin 321 is removed, and nut 318 is rotated to move locking dog 314 upwardly to progressively increase the load bearing against lower plate 306.

Referring to FIG. 11, to position upper plate 304, which carries force exerting means 326, pins 310 are removed and plate 304 is moved vertically by manually sliding plate 304 to the desired location along derrick legs 302 and then locked at that height by insertion of locking pins 310 through openings 308 of derrick legs 302 and blocks 312. Plate 304 is preferably provided with handles 307 to facilitate manual positioning thereof.

Alternatively, plate 304 can be raised or lowered to the desired position by releasing lock pins 310 from blocks 312 and holes 308 in legs 302 of derrick 300 and activating hydraulic cylinder 326 to extend ram 328 until end piece 332 bears against the top of a plate (not shown) or other suitable flat surface placed over the top of locking dog 314. Once end piece 332 encounters the plate, or is otherwise stopped from further downward movement as described below, the pins 310 in the blocks 312 of upper plate 304 are removed from legs 302 so that further extension of ram 328 raises upper plate 304 and hydraulic cylinder 328. Once upper plate 304 has reached the desired position, locking pins 310 are re-inserted through openings 308 in legs 302 and blocks 312, thus achieving selective positioning of upper plate 304 on derrick 300. Ram 328 need not bear against a plate resting on top of locking dog 314. All that is necessary is that ram 328 encounter resistance against continued extension. Resistance could be supplied by a block of wood, a push rod 346 or 350, a pin 310 placed in slot 334 in end 332, or even a pin or other convenient component placed in one of the holes 308 to prevent downward movement of ram 328.

Referring to FIG. 12A, once hydraulic cylinder 326 is positioned at the desired height, a force transmitting member such as push rods 346 or 350 is mounted on end piece 332. Mounting is accomplished by retracting ram 328 and lifting push rod 346 or 350 vertically into the space between end piece 332 and the top of locking dog 314. A pin 310 is inserted through the openings 348 and the lower end of push rod 346 or 350 is grasped in one hand while the top of push rod 346 or 350 is grasped with the other. Push rod 346 or 350 is then manually lifted and positioned so that the nose 343 of end piece 332 extends into the hollow end of the push rod 346 or 350. The openings 348 at the top of push rod 346 or 350 are then aligned with the slot 334 on end piece 332 and pin 336 is inserted. In the case of push rod 346, which is of the telescoping variety, the components 349', 349'', and 349''', etc., are restrained from telescoping movement by pin 347 extending through any suitable opening 348 therethrough.

Sample tube 340 or other member is attached to the lower end of push rod 346 or 350 directly or by means of the adapter ring 384 as shown in FIG. 14A. The "J" slots 364 of sample tube 340 are aligned with the pins 383 of adapter ring 384 and hydraulic cylinder 326 is then activated, and by extension of ram 328, sample tube 340 and push rod 346 or 350 are moved through the bore of locking dog 314 until contact with material such as the soil 204 is made. At this point, the top margin of push rod 346 or 350 and the shoulder 338 end piece 332 are aligned and seated as previously described. Further downward extension of ram 328 causes downward movement of push rods 346 or 350 and sample tube 340 into soil 204 along the line of action selected with derrick 300. That downward movement creates a reactive force equal and in the opposite direction to the driving force which tends to push derrick 300 in a direction opposite that line of action, i.e., at an angle away from the load bearing strata 102. Movement of derrick 300 is restrained, however, by engagement of derrick 300, particularly locking dog 314, with load bearing strata 102 by collar 200. The reactive forces resulting from the resistance of the soil to the forcing of the member through the material are thus transmitted from sample tube 340 to the hydraulic cylinder 326, to upper plate 304 across pins 310, into legs 302 of derrick 300, across pins 307 to lower plate 306, into locking dog 314 by bearing of lower plate 306 against nut 320, into collar 200, and through lip 218 into the discontinuity or groove 216 in load bearing strata 102. As noted above, those reactive forces can be transmitted to any material and/or load-bearing strata, or the material and strata can be one and the same.

As discussed previously, discontinuity 216 can be located at any point in the hole 110 in strata 102. In certain instances, it is desirable to locate discontinuity 216 at or near the bottom of hole 110. In such instances, there is no bottom surface of the discontinuity 216, or the strata 102 may be of insufficient thickness to develop the required strength, and downward forces on collar 200 cannot be effectively resisted in the manner described above. However, by action of axles 322 and wheels 320 or by pivoting of cams 306 into contact with strata 102, reactive forces can be effectively transmitted to the load bearing strata 102. In some applications, the reactive forces can be better transmitted to strata 102 by mounting a cylinder (not shown) having a radially extending plate at the bottom end thereof to the threads 320 in locking dog 314 in place of nut 319. The plate transmits force to strata 102 around the same radius as the force transmitted through the lip 218 of collar 200 and discontinuity 216, and the cylinder can be screwed downwardly into engagement with strata 102 to effectively place the portion of strata 102 between lip 218 and the plate in compression rather than tension. Such structure is particularly useful in applications in which the material comprising strata 102 is not compacted as, for instance, when strata 102 is itself the material through which the member is to be forced, e.g., the soil to be sampled.

Upon maximum extension of ram 328, further advancement of sample tube 340 is accomplished by extending the string of push rods 346 or 350. If a push rod of the type shown at reference numeral 346 is being used, ram 328 is retracted slightly, thus loosening the shear force on and allowing the removal of pin 347, and the portions 349', 349", and 349''', etc., are telescoped with respect to one another by further retraction of ram 328, causing section 349''' to be extended from the nested position within the other sections 349' and 349". The holes 348 in respective sections 349', 349", and 349''' are longitudinally aligned and pin 347 is reinserted, thus locking telescoping sections 349', 349", and 349''', together and resulting in an extension of the length of the push rod 346. Hydraulic cylinder 326 is then activated, further advancing sample tube 340 until additional extension is required. Retraction of the push rod 346 is performed in a similar manner, and a pin or anti-drop washer 370 is used for both extension and retraction to facilitate the handling of the string of members.

If a push rod of the type shown at reference numeral 350 is being used, ram 328 is also backed off slightly, a pin 310 or anti-drop washer 370 is inserted into one of the openings 358, and the pin 336 is then retracted from slot 334 and uppermost push rod 350. Ram 328 is then fully retracted, an additional push rod 350 is pinned to end piece 332, and ram 328 is extended until the pins 356 of the additional push rod 350 engage the J-slots 352 of the formerly uppermost push rod 350 resting on the top of locking dog 314. The string of push rods 350 extending down through hole 110 is then rotated with respect to the newly-added push rod 350 to lock onto that newly added push rod 350.

Sample tube 340 is advanced until the material or soil 204 fills the bore thereof or the desired sampling depth is reached, after which sample tube 340 is retracted. During retraction, the direction of the reactive forces is the reverse of the direction of those forces resulting from forcing the member into the soil 204, and referring to FIG. 12B, the reactive forces are transmitted through the legs 302 of derrick 300 and are transferred across axles 322 and through wheels 320 to the load bearing strata 102. As noted above, the legs 302 of derrick 300 are provided with cams 303, pivotally mounted to legs 302, which are pivoted into contact with load bearing strata 102 to function as load bearing members rather than wheels 320 and axles 322. Alternatively, the reactive forces resulting from retraction are transferred into the collar 200 in positive engagement with strata 102 by the nut 319 that is threaded onto locking dog 314 under and in contact with plate 306. A pin similar to pin 310 is inserted in an opening 308 just above lower plate 306 so that downward forces in the legs 302 of derrick 300 are transferred across pin 310 into lower plate 306 onto lower nut 319, into locking dog 314, through ears 316, into collar 200, and into load bearing strata 102 by means of lip 216 and discontinuity 218 when the cylindrical member is retracted.

Preferably, ram 328 is retracted only to a point at which a portion of the member such as sample tube 340, or a section 349', 349", or 349''' of push rod 346, or push rod 350, projects above the top of locking dog 314. Once that point is reached, the member is counter-rotated to disengage that member from the pins 356 (or 388 in the case of an adapter ring 384 mounted thereto). Rotation is faciliatated by insertion of pins similar to that shown at reference numeral 310 into the hole 341 of sample tube 340 or holes 348 of push rod 346 or 350, as the case may be. Pins 310 are used as a "cheater bar" for rotating the members for disengagement from each other and to prevent the member from falling back into the hole 110 once disengaged from adapter ring 384 or adjacent member. Once disconnected, push rod 346 or 350 is conveniently moved laterally by swinging on pin 336 or by movement of pin 336 in slot 334, so that the cylindrical member can be withdrawn without obstruction.

After removal of sample tube 340, anothe sample tube 340 is placed in the bore of locking dog 314 using a pin 310 or anti-drop washer 370 to prevent falling into that bore. Push rod 346 or 350 is swung into alignment with sample tube 340 and the adapter ring 384 is engaged thereto. The anti-drop washer 370 or pin 310 then is removed and hydraulic cylinder 326 activated to move sample tube 340 into contact with material 204 where sampling operations are resumed.

After the required number of material samples are obtained and sample tube 340 has been disengaged from adapter 352, the samples are removed from the bore of sample tube 340 as follows. The push rods 346 or 350 are released from end piece 332 and end piece 332 is unscrewed from the end of ram 328. Plunger 366 (see FIG. 15) is then screwed onto the threads 333 on the end of ram 328 and ram 328 is retracted all the way up into extruder head 360. A sample tube 340 containing a sample 368 therein is mounted to extruder head 360 by alignment of pins 362 with "J" slots 364 and then applying counter-rotation. Hydraulic cylinder 326 is then activated to advance plunger 366 against the material sample 368 contained within sample tube 340, thus extruding sample 368. Plunger 366 is then retracted, the now-empty sample tube 340 is removed from extruder head 360 and another sample tube 340 containing another sample is mounted thereto for repetition of that same process.

Although the invention has been described in terms of the above-characterized presently preferred embodiments, it will be understood by those skilled in the art who have the benefit of this disclosure that changes can be made to these embodiments without departing from the spirit and scope of the invention. It is envisioned that such changes would be included within the following claims.

What is claimed is:

1. An apparatus for forcing a member within a material comprising:
    means for selecting a line of action along which a member is to be forced within a material;
    means mounted to said line of action selecting means for forcing the member within the material along the line of action when activated;
    means positionable in a hole which extends only part way through the material within which the member is to forced for positively engaging the material within which the member is to be forced and having an opening therethrough for passage of the member when said member forcing means is activated; and
    means mounted to said line of action selecting means for engaging said material engaging means to resist movement of said line of action selecting means with respect to the material along the line of action upon activation of said member forcing means by transmitting to the material the reactive forces resulting from the forcing of the member within the material.

2. The apparatus of claim 1 wherein said material engaging means comprises a collar anchored in the material.

3. The apparatus of claim 2 wherein said means for engaging said material engaging means comprises a locking dog having means on one end thereof for releasably engaging said collar.

4. The apparatus of claim 3 wherein said line of action selecting means comprises a derrick having a first plate mounted thereto to which said member forcing means is mounted and a second plate mounted thereto between said first plate and said collar for engaging said locking dog.

5. The apparatus of claim 4 wherein said locking dog is provided with an opening therethrough for passage of the member when said member forcing means is activated.

6. The apparatus of claim 5 wherein said locking dog extends through a hole in said second plate.

7. The apparatus of claim 1 further comprising means mounted on said member forcing means for releasably mounting the member thereto.

8. The apparatus of claim 7 wherein said mounting means is provided with a shoulder for engaging the member and a taper for aligning the member on said shoulder when said member forcing means is activated.

9. The apparatus of claim 7 wherein said line of action selecting means comprises a derrick having a first plate mounted thereto, said member forcing means being mounted on said first plate.

10. The apparatus of claim 9 further comprising means for releasably mounting the member to said first plate to prevent movement of the member when said member forcing means is activated.

11. The apparatus of claim 10 wherein said member mounting means is mounted in a hole through said first plate and said member forcing means extends through said member mounting means when activated.

12. An apparatus for transmitting reactive forces to a strata exerted along a line of action at an angle with respect to the strata comprising:
    a collar for inserting into a hole in a strata having an outer surface shaped to approximate the shape of the hole;
    means formed in said collar for engaging an apparatus for exerting force along a line of action at an angle with respect to the strata in which the hole is located; and
    means on the outside surface of said collar for engaging a discontinuity in the wall of the hole to transmit the reactive force developed by the force exerting apparatus to which said collar is engaged to the strata in which the hole is located.

13. The apparatus of claim 12 additionally comprising means for expanding said discontinuity engaging means into said discontinuity.

14. The apparatus of claim 13 wherein said collar is comprised of first and second pieces, a portion of each of said first and second collar pieces being tapered for engaging said means for expanding said discontinuity engaging means.

15. The apparatus of claim 14 wherein said means for expanding said discontinuity engaging means comprises a tapered bushing for engaging the tapered portion of said first and second collar pieces.

16. The apparatus of claim 14 additionally comprising means for resisting movement of said first and second collar pieces away from each other when force is exerted by the force exerting apparatus to which said first and second collar pieces are engaged.

17. The apparatus of claim 12 wherein said discontinuity engaging means comprises an integral lip on the outside surface of said collar.

18. An apparatus for sampling a material under a load bearing strata comprising:
    a derrick for selecting a line of action and having first and second plates mounted thereto;
    selectively activatable means mounted to the first plate for forcing a sample tube mounted thereto into the material under the load bearing strata; and
    means having an opening therethrough for passage of the sample tube when said sample tube forcing means is activated extending through a hole in said second plate for positively engaging a hole within the load bearing strata to transmit to the material the reactive forces resulting from the forcing of the sample tube into the material upon activation of said sample tube forcing means to force the sample tube mounted thereto into the material, thereby preventing movement of said derrick with respect to the load bearing strata.

19. The apparatus of claim 18 additionally comprising means on the upper plate for preventing movement of the sample tube with respect to the upper plate upon activation of said sample tube forcing means.

20. The apparatus of claim 19 wherein said sample tube forcing means is provided with a plunger releasably mounted thereto for forcing samples of the material into which the sample tube is forced out of the sample tube when said sample tube forcing means is activated.

21. A method of forcing a member within a material wherein the material either comprises a load bearing strata or is covered by a load bearing strata comprising:
  removing material from the wall of a hole in a load bearing strata, the load bearing strata either comprising the material within which a member is to be forced or having a material thereunder within which a member is to be forced to create a discontinuity in the wall of the hole;
  inserting a collar into the hole in the strata, the collar having means on the outside surface thereof for engaging the discontinuity in the wall of the hole;
  passing a member through the hole and into engagement with either the material comprising the strata in which the collar is engaged or the material under the strata in which the collar is engaged for forcing within the material; and
  transmitting the reactive force resulting from the forcing of the member within the material to the strata.

22. An apparatus for forcing a member within a material comprising:
  means for selecting a line of action along which a member is to be forced within a material, the material either comprising a load bearing strata or being covered by a load bearing strata;
  means mounted to said line of action selecting means for forcing the member within the material along the line of action when activated;
  means positionable in a hole in the load bearing strata which either comprises or covers the material within which the member is to be forced for positively engaging the load bearing strata and having an opening therethrough for passage of the member when said member forcing means is activated; and
  means mounted to said line of action selecting means for engaging said load bearing strata engaging means to resist movement with respect to the load bearing strata along the line of action upon activation of said member forcing means by transmitting reactive forces resulting from the resistance of the material to the forcing of the member into the load bearing strata.

* * * * *